US009270080B1

(12) United States Patent
Clowes et al.

(10) Patent No.: US 9,270,080 B1
(45) Date of Patent: Feb. 23, 2016

(54) METHODS AND APPARATUS PERTAINING TO THE USE AND GENERATION OF BROADBAND LIGHT (75) Inventors: John Clowes, Lymington (GB); Christophe Codemard, Eastleigh (GB); Adam Devine, Southampton (GB)

(73) Assignee: Fianium Ltd, Southampton (GB)

( * ) Notice: Subject to any disclaimer, the term of this patent is extended or adjusted under 35 U.S.C. 154(b) by 771 days.

(21) Appl. No.: 13/524,817

(22) Filed: Jun. 15, 2012

Related U.S. Application Data (60) Provisional application No. 61/501,219, filed on Jun. 26, 2011.

(51) Int. Cl.
*H01S 3/30* (2006.01)
*H01S 3/094* (2006.01)
*G02F 1/35* (2006.01)

(52) U.S. Cl.
CPC ........... *H01S 3/302* (2013.01); *H01S 3/094003* (2013.01); *G02F 2001/3503* (2013.01); *G02F 2001/3528* (2013.01)

(58) Field of Classification Search
CPC .............. G01F 1/35; G02F 2001/3503; G02F 2001/3528; H01S 3/30; H01S 3/302; H01S 3/094049; H01S 3/094046; H01S 3/094042; H01S 3/094003
See application file for complete search history.

(56) References Cited

U.S. PATENT DOCUMENTS

| | | | | |
|---|---|---|---|---|
| 4,815,079 A * | 3/1989 | Snitzer et al. | ..................... | 372/6 |
| 5,864,644 A * | 1/1999 | DiGiovanni et al. | ........... | 385/43 |
| 5,999,548 A * | 12/1999 | Mori et al. | ....................... | 372/22 |
| 5,999,673 A * | 12/1999 | Valentin et al. | .................. | 385/43 |
| 6,434,295 B1 * | 8/2002 | MacCormack et al. | ........ | 385/27 |
| 6,434,302 B1 * | 8/2002 | Fidric et al. | ...................... | 385/43 |
| 6,826,335 B1 * | 11/2004 | Grudinin et al. | ................. | 385/43 |
| 7,447,408 B2 * | 11/2008 | Bouma et al. | ................. | 385/123 |
| 7,769,298 B2 * | 8/2010 | Igarashi et al. | ............... | 398/146 |
| 7,859,679 B2 * | 12/2010 | Bouma et al. | ................. | 356/479 |
| 7,903,697 B2 * | 3/2011 | Murison et al. | .................... | 372/6 |
| 8,345,348 B1 * | 1/2013 | Savage-Leuchs | .......... | 359/341.1 |
| 8,385,699 B2 * | 2/2013 | Liu | ................................ | 385/42 |
| 8,982,918 B2 * | 3/2015 | Pedersen | .................... | 372/38.01 |
| 2008/0106786 A1 | 5/2008 | Nagasawa et al. | | |

(Continued)

FOREIGN PATENT DOCUMENTS

WO    WO2010/001165 A1    1/2010

*Primary Examiner* — John Lee
(74) *Attorney, Agent, or Firm* — Peter Rainville (57) ABSTRACT

A broadband light source (e.g., an optical supercontinuum apparatus), can comprise a pump laser; a non-linear optical element configured for generating spectrally broadened light generated responsive to receiving pump laser pulses and one or more non-linear processes; an optical output for delivering spectrally broadened light to a target; a length of optical waveguide optically upstream of the output and in optical communication therewith; and a sensor apparatus. The length of optical waveguide can comprise at least a first waveguiding region configured for propagating spectrally broadened light in a forward direction toward the output and can be further configured for receiving backward propagating light responsive to the forward propagating light. The sensor apparatus can be configured for optical communication with the length of optical waveguide so as to sense the backward propagating light propagated by the length of optical waveguide. Methods for operating and using such broadband light source are disclosed, as are applications of the methods and apparatus.

30 Claims, 5 Drawing Sheets

(56) References Cited

U.S. PATENT DOCUMENTS

| | | |
|---|---|---|
| 2008/0232406 A1* | 9/2008 | Nicholson et al. ............ 372/4 |
| 2009/0028193 A1* | 1/2009 | Islam ............................ 372/6 |
| 2009/0095023 A1* | 4/2009 | Dong et al. .................. 65/393 |
| 2009/0152475 A1* | 6/2009 | Sasaki et al. ............ 250/492.1 |
| 2010/0142959 A1* | 6/2010 | Futami et al. ................ 398/79 |
| 2010/0272129 A1* | 10/2010 | Harter et al. ................. 372/6 |
| 2011/0002585 A1 | 1/2011 | Gibson et al. |
| 2011/0091155 A1* | 4/2011 | Yilmaz et al. ............... 385/30 |
| 2011/0194812 A1* | 8/2011 | Melin et al. ................. 385/27 |
| 2011/0284510 A1 | 11/2011 | Reeves-Hall |
| 2012/0027031 A1* | 2/2012 | Liu ................................ 372/6 |
| 2013/0301663 A1* | 11/2013 | Clowes et al. ................ 372/6 |
| 2014/0168755 A1* | 6/2014 | Clowes et al. ........... 359/341.1 |
| 2014/0218789 A1* | 8/2014 | Clowes et al. .............. 359/326 |
| 2014/0233091 A1* | 8/2014 | Clowes et al. ........... 359/341.1 |
| 2014/0368900 A1* | 12/2014 | Pan et al. .................... 359/326 |
| 2014/0369370 A1* | 12/2014 | Clowes et al. ............... 372/21 |
| 2015/0055962 A1* | 2/2015 | Clowes et al. .............. 398/201 |

* cited by examiner

METHODS AND APPARATUS PERTAINING TO THE USE AND GENERATION OF BROADBAND LIGHT

CROSS REFERENCE TO RELATED APPLICATIONS

The present application claims priority under 35 U.S.C. §119(e) to U.S. Provisional Patent Application Ser. No. 60/501,219, entitled "Methods and Apparatus Pertaining to the Use and Generation of Broadband Light", filed 26 Jun. 2011. The foregoing application is incorporated by reference herein.

FIELD OF THE INVENTION

The present invention relates to methods and apparatus for using and producing broadband laser light and to sources of such light, such as, for example, supercontinuum optical sources, and applications involving the foregoing.

BACKGROUND

Supercontinuum fiber lasers, such as those available from Fianium Ltd. of Southampton, UK (e.g., models SC400 and SC450, see www.fianium.com) can deliver "white" or broad bandwidth laser light. A highly non-linear optical medium is pumped with intense laser pump light (usually pulses of light) to generate the supercontinuum.

In certain supercontinuum lasers commercially available today, such as the SC400 and SC450, the source of intense laser pump light is typically a pulsed or ultrafast fiber-delivered laser and the non-linear optical medium is a highly non-linear optical fiber such as a photonic crystal fiber. The output of the pump laser and non-linear fiber are fusion spliced together to produce a homogeneous, continuous optical fiber. This configuration has advantages over free space launching of the pump light into the non-linear fiber through combinations of lenses in terms of reliability and mechanical robustness.

It can be of interest to sample the output of the supercontinuum laser. Such sampling can be desirable, for example, to achieve closed loop control or to monitor the output power to check for degradation or a break in the delivery fiber. Such a break could constitute a safety hazard, and it is preferable than a means is in place for detecting the break. As another example, sampling can often be useful for analyzing or monitoring of the spectral content of supercontinuum or filtered supercontinuum light delivered by an optical fiber. In-situ analysis or monitoring can be used for spectral characterization for real-time calibration of the source or of the illumination light beam when incorporated into instrumentation or experiments.

The output light can be sampled using free space techniques. A partial beam splitter or partially reflective surface can split off a portion of a free space beam, and the split beam can be analyzed using a spectrometer, CCD array, etc. Free-space sampling of the laser output is not convenient for many fiber-based applications, as often a free space beam is only available at the output of the delivery fiber of the supercontinuum source, which is typically positioned remotely from the laser source that houses the electronics and sources of electrical power.

Accordingly, it is an object of the invention to address one or more of the deficiencies of the prior art.

SUMMARY OF THE INVENTION

In one aspect, the disclosure provides an optical supercontinuum apparatus comprising a pump laser for providing pump pulses; a non-linear optical element configured for generating spectrally broadened light responsive to the pump pulses and one or more non-linear processes; an optical output for delivering spectrally broadened light to a target; a length of optical waveguide optically upstream of the output and in optical communication therewith; and sensor apparatus configured for optical communication with the length of optical waveguide. The length of optical waveguide can comprise at least a first waveguiding region configured for propagating spectrally broadened light in a forward direction, the forward direction being toward the output. The length of optical waveguide can be further configured for receiving backward propagating light responsive to the forward propagating light, "backward" meaning being in a direction opposite to the forward propagating light. The sensor apparatus can be configured for optical communication with the length of optical waveguide so as to sense the backward propagating light propagated by the length of optical waveguide.

In other aspects of the disclosure, the non-linear optical element can comprise the length of optical waveguide. The length of optical waveguide can comprise a second waveguiding region that is different than the first waveguiding region, where the second waveguiding region can receive and propagate the backward propagating light. The second waveguiding region may be configured to support substantially more spatial modes than the first waveguiding region. The length of optical waveguide may comprise a double clad fiber having a core, an inner cladding disposed about the core, and an outer cladding disposed about the inner cladding. The first waveguiding region may comprise the core and the second waveguiding region may comprise the inner cladding. The first waveguiding region may be single mode over at least part of (e.g., a majority of) the full width half maximum (FWHM) wavelength range of the spectrum of spectrally broadened light generated by the non-linear optical element and the second waveguiding region can be multimode over at least part of (e.g., at least a majority of) the same wavelength range. The second waveguiding region may have a numerical aperture of at least 0.4. The material of the first and second waveguiding regions may consist essentially of undoped silica glass. The optical supercontinuum apparatus may be configured such that the length of optical waveguide spectrally broadens light propagated thereby in the forward direction. The length of optical waveguide can comprise at least one more cladding than the non-linear optical element.

The optical supercontinuum apparatus can comprise an optical element that serves as both the non-linear optical element and as the length of optical waveguide. The nonlinear optical element can comprise a selected length of optical fiber and the length of optical waveguide can comprise the selected length of optical fiber.

In yet further aspects of the disclosure, the sensor apparatus may comprise a photodetector or an optical spectrum analyzer. The pump laser can comprise a pulsed fiber laser producing pump pulses having a FWHM time duration that is in the range from 1 ps to 500 ps. The pump laser can comprise a fiber laser cavity comprising a semiconductor saturable absorber (SESAM) mode-locking element and a length of rare earth doped optical fiber. The length of rare earth doped optical fiber can have normal dispersion at its wavelength of operation.

In additional aspects of the disclosure, the non-linear optical element can comprise a length of microstructured fiber having a core and a plurality of longitudinally extending features disposed about the core. In certain practices, the microstructured optical fiber does not guide light via a photonic bandgap effect and/or the core does not comprise an endlessly single mode core. The core can guide light via the phenomenon of total internal reflection. The core of the microstructured optical fiber comprises a diameter of no less than 2 microns and no greater than 6 microns and a numerical aperture of no less than 0.12 and no greater than 0.35 and wherein the microstructured region disposed about the core comprises an air-fill fraction of at least 0.5. The non-linear optical element can comprise a length of optical fiber, and the apparatus can be configured such that the length of optical waveguide propagates forward propagating light in substantially more spatial modes than the length of optical waveguide. The length of optical fiber can propagate spectrally broadened light in substantially a single spatial mode.

The optical supercontinuum apparatus can comprise an optical fiber combiner optically interposed between the length of optical waveguide and the sensor apparatus and configured for coupling backward propagating light from the length of optical waveguide for provision to the sensor apparatus. The optical fiber combiner can comprise first and second optical fiber legs arranged in a feedthrough configuration and at least one side coupling optical fiber leg. The side coupling optical fiber leg can be in optical communication with the non-linear optical element for receiving spectrally broadened light and coupling the spectrally broadened light to the first optical fiber leg, and the first optical fiber leg can be in optical communication with the length of optical waveguide and the second optical fiber leg can be in optical communication with the sensor apparatus.

In certain aspects the present disclosure describes configurations of laser systems wherein the output of the laser (broadband or following filtration) is delivered through an optical fiber or optical fiber component having a double-clad structure to enable collection and analysis of reflected light from the optical fiber or an external surface as backward propagating light. The backward propagating light can be analyzed in terms of one or more optical properties (e.g., power, spectral content, phase, etc.) to, for example, monitor the status of the laser source, provide feedback control, allow safety interlocking or to analyze a sample under investigation, such as by measuring interference patterns used for film thickness or high resolution distance measurement.

The present disclosure also teaches methods, such as methods of making and using the apparatus and systems taught herein, which will be evident to one of ordinary skill upon study of the present disclosure.

As one example, in one aspect the disclosure teaches a method of operating a source of supercontinuum laser pulses, comprising optically pumping a length of optical fiber with optical pump pulses to generate spectrally broadened light via one or more non-linear processes; propagating the spectrally broadened light in the forward direction along a length of optical waveguide for eventual delivery to an output; receiving, responsive to the forward propagating spectrally broadened light, backward propagating light with length of optical waveguide; and sensing the backward propagating light with a sensor apparatus in optical communication with the length of optical waveguide so as to receive backward propagating light. The method can comprise redirecting, optically upstream of the output, forward propagating spectrally broadened light so as to become backward propagating and wherein at least the majority of the optical power sensed by the sensor apparatus is due to such redirected forward propagating light. The method can include changing a property of the spectrally broadened light output from the output responsive to the sensing of the backward propagating light.

In other aspects of the disclosure, sensing the backward propagating light can comprise sensing the backward propagating light so as to determine a property of the forward propagating spectrally broadened light. Optically pumping the length of optical fiber can comprise optically pumping the length of optical fiber with pulses having a time duration in the range from 1 ps to 250 ps, a wavelength in the range from 900 nm to 1200 nm, and wherein the length of optical fiber comprises a zero dispersion wavelength in the range of 900 nm to 1200 nm. Propagating spectrally broadened light in the forward direction can comprise propagating the spectrally broadened light with a first waveguiding region of the length of optical waveguide and wherein receiving the backward propagating light comprises receiving the backward propagating light with a second waveguiding region of the length of optical waveguide, wherein second waveguiding region does not substantially propagate forward propagating spectrally broadened light. Receiving backward propagating light can comprise receiving backward propagating light from a target to which light from the output has been directed.

Light, as that term is used herein, is not understood to be limited to visible light but is used in the broader sense of optical electromagnetic energy. Spectrally broadened light means light having a wavelength generated or amplified by a non-linear spectral broadening process, such as, for example, self phase modulation. Pumping the non-linear optical element initiates this process of spectral broadening.

As one of ordinary skill readily appreciates from a consideration of the present disclosure, the spectrally broadened light in some aspects of the invention can comprise wavelengths from below 400 nm to at least 2000 nm. However, in various practices of the disclosure, the spectrally broadened light, as it propagates along at least some portion of the non-linear optical element and/or of the length of optical waveguide, and/or as it is output from the laser apparatus, can comprise a wavelength spectrum having a FWHM bandwidth of at least 10 nm; at least 50 nm; at least 100 nm; at least 250 nm; at least 500 nm; at least 750 nm; at least 1000 nm; at least 1250 nm; at least 1500 nm; or at least 1750 nm.

The bandwidth of the spectrally broadened light can vary at different locations, particularly, of course, if the light is filtered before it reaches the output of the laser apparatus. For example, the spectrally broadened light as output from the output can, in certain circumstances, have a relatively narrow spectral bandwidth, even perhaps a spectral bandwidth as narrow as or narrower than that of the pump light. This is simply because a filter, such as an acousto-optic tunable filter, can be interposed optically upstream of the output so as to allow a user to select a desired wavelength or wavelengths to be output by the output.

Backward propagating light comprises light received by the length of optical waveguide so as to propagate in the opposite direction of the forward propagating light. The backward propagating light can be received responsive to the forward propagating spectrally broadened light via one or more of a number of possible mechanisms. For example, the backward propagating light can comprise spectrally broadened light that exits the output and is reflected, refracted, diffracted or scattered from a target, a lens or other part of the beam delivery optic, or even from within the length of optical waveguide or from a part thereof. For example, the length of optical waveguide can include a fiber grating, such as a long period grating, that is disposed so as to direct forward propagating light in the core into backward propagating light in the inner cladding of the double clad fiber. As another example, the backward propagating light can be reflected from, for example, the end face of the length of optical waveguide, such as an angled end face that creates a Fresnel reflection of light from the first waveguiding region into the second waveguiding region. As another example, the backward propagating can be other than light directly reflected or scattered from a target. A target could fluoresce responsive to the target receiving light from the first waveguiding region, and some of the light from the fluorescence can be received and backward propagated by the second waveguiding region.

As used herein, the term "photodetector" includes an element that, responsive to receiving light, provides an output (e.g., an electrical output, such as a voltage or current) that is responsive to a selected property of the light (e.g., intensity). A photodetector can include, for example, a photodiode, phototransistor, photovoltaic cell or charge coupled device (CCD).

Not every component is labeled in every one of the foregoing FIGURES, nor is every component of each embodiment of the invention shown where illustration is not considered necessary to allow those of ordinary skill in the art to understand the invention. The FIGURES are schematic and not necessarily to scale.

When considered in conjunction with the foregoing FIGURES, further features of the invention will become apparent from the following detailed description of non-limiting embodiments of the invention.

DETAILED DESCRIPTION

Figure 1:
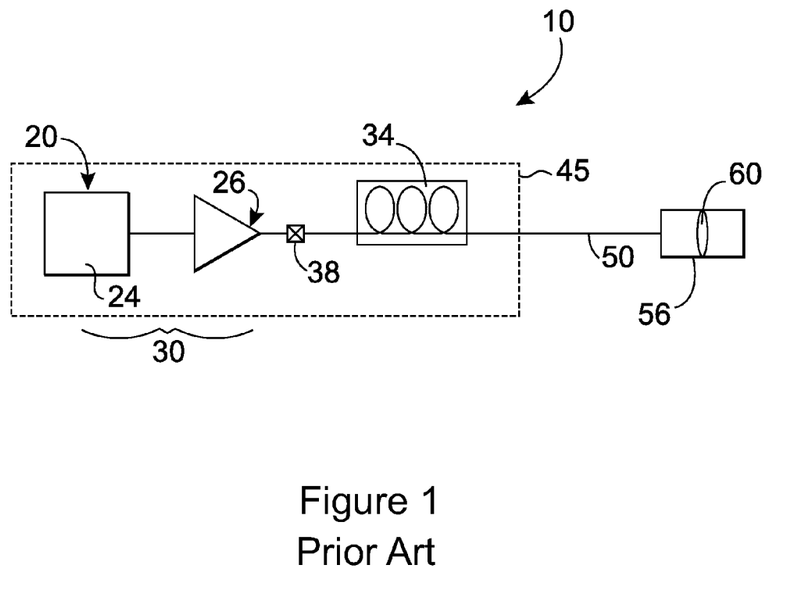
FIG. 1 schematically illustrates a prior art supercontinuum system.

FIG. 1 shows one example of a prior art supercontinuum laser light source 10. The supercontinuum laser light source 10 comprises a seed source 20, which in FIG. 1 comprises a modelocked optical fiber oscillator 24, which delivers short pulses of light at approximately 1064 nm wavelength. These pulses are amplified to higher peak powers in an optical fiber amplifier 26 (e.g., an ytterbium-doped fiber amplifier). A seed source 20 in combination with amplification (via, for example, one or more fiber amplifiers) optically downstream from the seed source 20 is commonly termed a Master Oscillator Power Amplifier (MOPA), and is indicated by reference numeral 30 in FIG. 1.

The MOPA 30 pumps a highly non-linear optical fiber 34 with a stream of high peak-power optical pulses. The MOPA 30 can include an output fiber spliced to the highly non-linear fiber 34 via splice 38 so as to make the whole system 10 ultra-reliable and robust. Within the non-linear optical fiber 34 the high peak power pump pulses undergo spectral broadening due to a combination of non-linear optical effects, which can include, for example, self-phase modulation. Depending on the design of the supercontinuum laser light source 10, the non-linear optical fiber 34 can output a stream of optical pulses having an ultra wide optical spectral bandwidth. For example, the optical spectral bandwidth can cover a range extending from the UV/Blue region of the spectrum (below 400 nm) to the short wavelength infra-red region (>2000 nm).

In many commercial systems or in instruments in which the supercontinuum laser 10 is integrated, the MOPA 30, splice 38 to the non-linear fiber 34 and the input end of the non-linear fiber are often positioned (for reasons of integration and safety) within a laser chassis 45. However, the output end of the laser delivery fiber 50 (which often comprises a non-linear optical fiber that provides spectrally broadening) is positioned remotely from laser chassis 45. This allows for remote delivery of the laser light from a very compact output or beam delivery optic 56, often comprising no more than an optical window or a collimating lens 60 to collimate the divergent beam from the optical fiber into a collimated beam.

It is often desirable or necessary to monitor the output of a light source such as the supercontinuum fiber laser source 10. In most fiber-based laser sources it is common to use a fiber-optic tap coupler to sample the laser output prior to delivery to the delivery fiber. The tap coupler splits off a small amount of power from the core of a fiber propagating the laser light, so as to, for example, monitor the laser output power or spectrum or to provide a control signal for closed-loop power control. Such an arrangement can be problematic for some supercontinuum systems. Tap couplers are typically spectrally narrowband and hence may sample only some of the broadband light output by a supercontinuum laser light source having a larger spectral output bandwidth. Furthermore a narrowband tap coupler can act as a spectral filter in transmission, reducing the spectral breadth of the light output from certain supercontinuum systems. Tap couplers work fine with most lasers because the lasers provide only spectrally narrowband output light.

In another approach, the beam delivery optic 56 can include a sensor apparatus, such as a photodiode, positioned so as to receive light either scattered or partially split off from the free-space output beam. However, this approach can require a relatively large beam delivery optic and electrical power delivery to the beam optical and/or communication between the sensor apparatus and the chassis, and hence also be problematic or undesirable.

Nevertheless, monitoring the output power can be required for laser safety, such as to ensure the integrity of the delivery fiber from the chassis 45 to the beam delivery optic 56. Furthermore, for ultimate stability of the supercontinuum light source 10 it is beneficial to be able to have power and preferably spectral information about the light delivered by the source, such that the system can be closed loop or that the spectral information can be utilised for real-time calibration.

Figure 2:
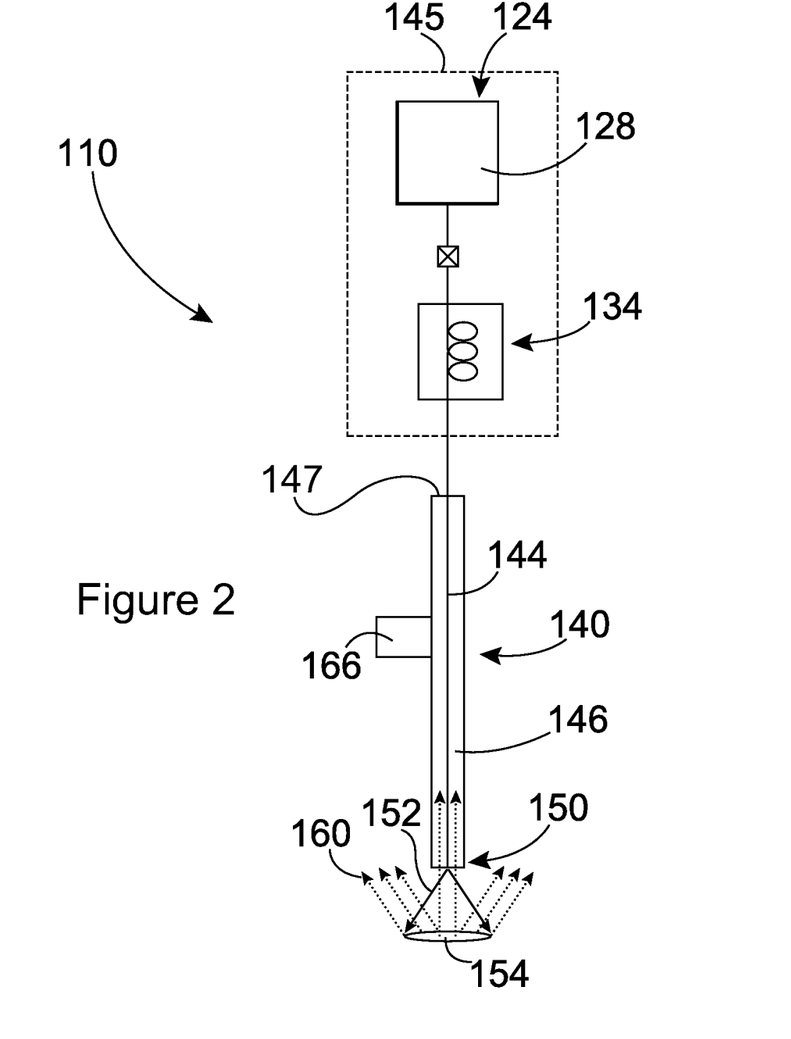
FIG. 2 schematically illustrates one embodiment of the present invention.

FIG. 2 schematically illustrates one embodiment of the present invention. FIG. 2 shows a supercontinuum laser light source 110 comprising a fiber delivered pump laser source 124 (e.g., MOPA 30 of FIG. 1, indicated schematically by reference numeral 128) in optical communication with a non-linear element 134, which can comprise a length of optical fiber. The pump laser source 124 pumps the non-linear optical element 134, which then spectrally broadens the output of the pump laser source 124 via one or more non-linear processes to output spectrally broadened output pulses. The non-linear element 134 is in optical communication with a length of optical waveguide 140, which can comprise a length of optical fiber. The length of optical waveguide 140 can include first and second waveguiding regions, 144 and 146, respectively. Spectrally broadened light is delivered to the first waveguiding region 144 at the proximate end 147 of the length of optical waveguide 140 for propagation to a distal end 150 thereof.

As is explained in more detail below, the second waveguiding region 146 typically propagates backward propagating light, that is, the second waveguiding region guides light that is propagating in a direction away from the distal end 150 and toward the proximate end 147 (though the light need not originate at the distal end 150 nor actually reach the proximate end 147). Where the length of optical waveguide 140 comprises different first and second waveguiding regions for separately propagating the forwardly and backward propagating light, the non-linear element 134 is typically not in optical communication with second waveguiding region 146 at the proximate end 147 of the length of optical waveguide 140 for delivery of broadened light to the second waveguiding region 146.

The spectrally broadened light can exit the length of optical waveguide as an optical beam 152. The beam can be directed to a target 154. The second waveguiding region 146 of the length of optical waveguide can receive scattered (e.g., reflected) light, such as light 160 scattered from the target 154, which is then guided by the second waveguiding region 146 and backwards propagates along the length of optical waveguide. The second waveguiding region 146 can propagate light in the opposite direction as compared to the spectrally broadened light propagated by the first waveguiding region 144.

A sensor apparatus 166 is provided in optical communication with the second waveguiding region 146 for sensing backward propagating light propagating in the second waveguiding region. The sensor apparatus 166 can be configured to sense one or more optical properties of the backward propagating light. The sensor apparatus 166 can comprise a photodiode, a phototransistor or a more sophisticated optical diagnostic component for analyzing the backward propagating light, such as, for example, an optical spectrum analyzer, CCD array, spectrometer or interferometer. Such sensor apparatus can be used, for example, for monitoring or recording the optical intensity, phase or spectrum of the backward propagating light. Optical communication between the sensor apparatus 166 and the second waveguiding region 146 can be effected in a variety of ways. For example, as shown in FIG. 2, the sensor apparatus 166 can be in physical contact with an outer cladding (which can be a coating) of the length of optical waveguide 140 and configured to interact with the evanescent field of the backward propagating light. Other techniques are known as well. For example, the length of optical waveguide 140 can be bent so that backward propagating light exceeds the acceptance angle of the second waveguiding region and exits a side of the length of optical waveguide for reception by the sensor apparatus 166.

The second waveguiding region 146 can be configured to have a large numerical aperture (e.g. 0.5 or even greater) and waveguide diameter for facilitating capturing scattered or reflected light. The laser chassis 145 can include the fiber delivered pump laser source 128 and nonlinear element 134. The distal end 150 of the length of optical waveguide 140 can be remotely located relative to the laser chassis 145.

Figure 3A:
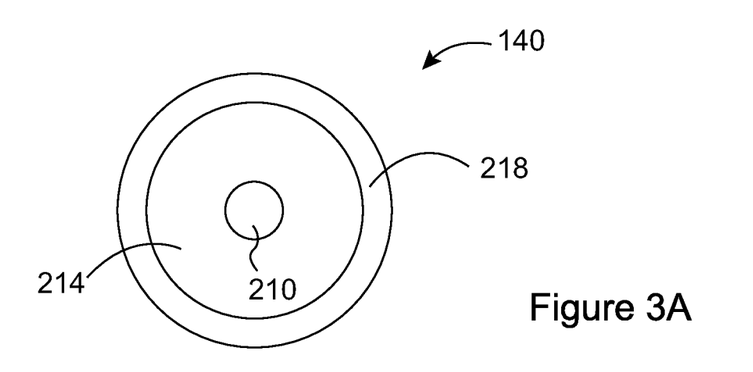
FIG. 3A schematically illustrates one example of length of optical waveguide comprising first and second waveguiding regions.

FIG. 3A schematically illustrates a cross section of one example of a length of optical waveguide 140 comprising first and second waveguiding regions. In the embodiment shown in FIG. 3A, the length of optical waveguide 140 comprises a double clad optical fiber having a core 210, an inner cladding 214 disposed about the core 210, and a second cladding 218 disposed about the inner cladding 214. The inner cladding 214 can have a first selected numerical aperture relative to the core 210, and the second cladding 218 can have a second selected numerical aperture relative to the inner cladding 214. Typically the inner cladding 214 has a lower effective refractive index than the core 210 and the second cladding 218 has a lower effective refractive index than the inner cladding 214.

Figure 3B:
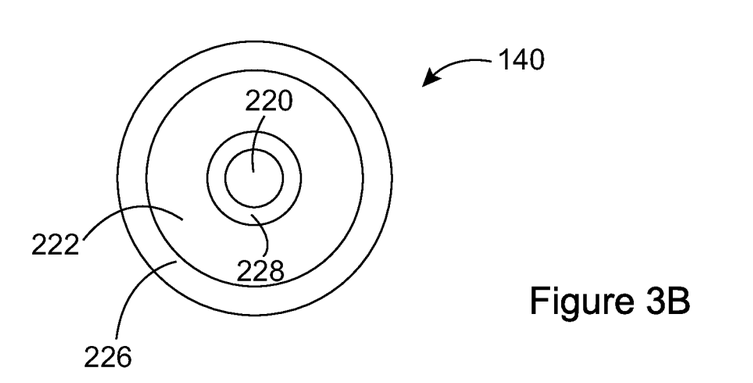
FIG. 3B schematically illustrates another example of length of optical waveguide comprising first and second waveguiding regions.

FIG. 3B schematically illustrates another example of length of optical waveguide 140. The length of optical waveguide 140 of FIG. 3B is substantially similar to that of FIG. 3A, and comprises a double clad optical fiber having a core 220, an inner cladding 222 disposed about the core 220, and a second cladding 226 disposed about the inner cladding 222. Typically the inner cladding 222 has a lower effective refractive index than the core 220 and the second cladding 226 has a lower effective refractive index than the inner cladding 222. However there is also included a region 228 disposed between the inner cladding 222 and the core 220 and which can have an effective refractive index that is less than that of the core 220 and/or the inner cladding 222 or both. The core 220 and inner cladding 222 can comprise substantially undoped silica and the region 228 can comprise down doped silica glass, such as, for example, fluorine doped silica glass.

Figure 3C:
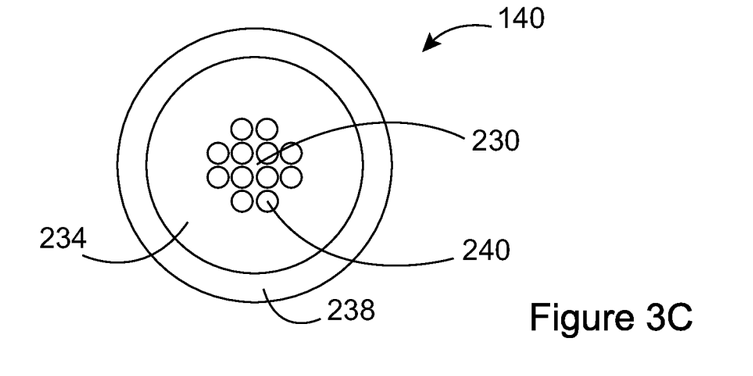
FIG. 3C schematically illustrates another example of length of optical waveguide comprising first and second waveguiding regions.

FIG. 3C schematically illustrates another example of a length of optical waveguide comprising first and second waveguiding regions. In FIG. 3C the length of optical waveguide 140 comprises a microstructured double clad optical fiber comprising a core region 230, an inner cladding 234 disposed about the core region 230, and second cladding 238 disposed about the inner cladding 234. The microstructured region 240 can comprise a plurality of longitudinally extending features (e.g., voids or air holes) that are configured to confine light to the core region 230. Such a fiber as shown in FIG. 3C can also be referred to as a holey or photonic crystal fiber. The second cladding 238 can have a lower effective refractive index than that of the inner cladding 234. As with the double clad fibers shown in FIGS. 3A and 3B, the second cladding 238 can comprise a low index coating applied to the fiber during the draw process.

The term "double clad" as used herein means a fiber having two or more claddings, wherein cladding is a region that acts to tend to confine light to a region about which the cladding is disposed. Optical elements, such as fibers, can include coatings and jackets that may or may not also act as claddings. A cladding typically has a lower effective refractive index than the region about which it is disposed and to which it is intended to confine light. In the double clad fibers shown above the first waveguiding region 144 of the length of optical waveguide 140 can comprise the core (210, 220, 230) of the double clad fiber and the second waveguiding region 146 can comprise the inner cladding (214, 222, 234). Typically the core or core region of the double clad fiber is substantially free of a rare earth dopant. The core region of the double clad fibers described herein can be nonlinear for providing the spectral broadening of light described herein.

The first or inner cladding of a double clad fiber can have a relatively large numerical aperture and cross sectional area as compared to other regions of a double clad fiber for better collecting backward propagating light, such as, for example, light scattered or otherwise obtained from a target, collimating lens of beam delivery optic, etc. The ratio of an outer diameter of an inner cladding to the outer diameter of a core or core region of a double clad fiber (the ratio is indicative of the ratio of cross sectional areas) can be at least 8; at least 10; at least 15; at least 25; or at least 40. The numerical aperture of the inner cladding can be at least 0.4; at least 0.45; at least 0.5, or even at least 0.55.

With reference again to FIG. 2, the length of optical waveguide 140 can be arranged optically downstream of the non-linear element 134. Preferably, optical communication is effected between the non-linear optical element 134 and the length of optical waveguide 140 without any substantial use of free space transmission. For example, the non-linear optical element 134 and the length of optical waveguide 140 can comprise a continuous length of optical fiber that may or may not include a splice. The length of optical waveguide can have substantially the same optical properties as a length of optical fiber comprised by the nonlinear optical element and, additionally or alternatively, the optical properties can remain substantially the same along the length of optical fiber of the optical waveguide. The length of optical waveguide can be designed to have non-linear properties, in which case the optical waveguide can also provide spectral broadening as well as guide light to the output. The nonlinear optical element 134 can comprise a double clad fiber, such as fiber having substantially or generally the same construction as the fiber of the length of optical waveguide 140, and can have a nonlinear core for providing the spectral broadening noted herein. The second cladding of the double clad fiber of the nonlinear optical element 134 can guide backward propagating light received from the target to an appropriate sensor. The nonlinear core can be single mode for a selected wavelength or wavelengths, such as at the pump wavelength or over at least part of the FWHM wavelength range of the spectrally broadened light.

In certain practices of the invention, the nonlinear optical element 134 and the length of optical waveguide 140 comprise different elements that have distinguishable features. For example, the nonlinear optical element 134 can comprise a length of single clad optical fiber and the length of optical waveguide 140 can comprise a length of double clad fiber (which may or may not provide additional spectral broadening). As another example, the nonlinear optical element 134 can comprise a length of optical fiber having a tapered core and the length of optical waveguide can comprise a length of optical fiber having a core having a substantially constant cross sectional area. In other practices of the invention, however, the nonlinear optical element 134 and the length of optical waveguide 140 can comprise the same optical element. For example, the length of optical waveguide 140 can include a length of optical fiber that is configured to produce spectrally broadened light from the pump pulses from the pump laser source 124. In certain practices there need not be any other element, such as a separate optical element upstream of the length of optical fiber, that provides any substantial spectral broadening. In some practices of the invention a length of nonlinear optical fiber that spectrally broadens pump pulses can serve both as the length of optical waveguide 140 and as the nonlinear optical element 134. The foregoing considerations apply to the embodiment shown in FIG. 2, as well, as one of ordinary skill will readily perceive based on the disclosure herein, to other embodiments disclosed herein as well. Generally speaking, it is understood that the features disclosed in conjunction with one embodiment can be included with another embodiment even if not explicitly shown in conjunction with the other embodiment.

The length of optical waveguide 140 can comprise a waveguiding region that both receives forward propagating light for delivery to the output and backward propagating light radiation, such as, for example, forward propagating light radiated from an output and reflected from the target back into the waveguiding region. For example, the length of optical waveguide 140 can comprise a fiber having a multi-mode core wherein the multimode core is configured to both propagate spectrally broadened light in the forward direction and receive backward propagating light.

Figure 4:
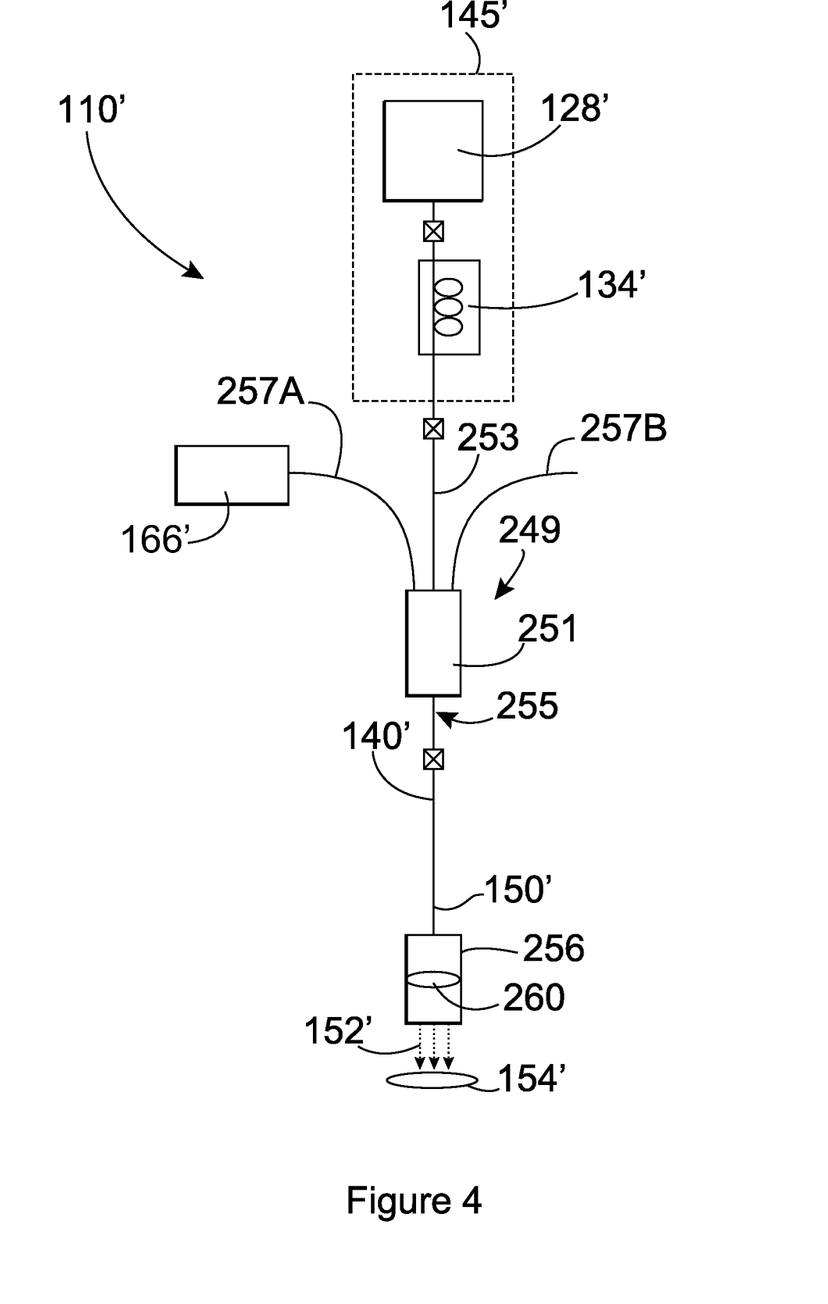
FIG. 4 schematically illustrates another example of an embodiment of the invention.

FIG. 4 schematically illustrates another example of a supercontinuum laser light source 110' according to an embodiment of the invention. The light source 110' can be the same as that described above, as indicated by the use of the same reference numerals (distinguished with primes), with certain distinctions now discussed. The light source 110' can include an optical fiber combiner 249. The optical fiber combiner 249 can include a combiner section 251 joining an input optical fiber leg 253, an output optical fiber leg 255, and one or more coupling optical fiber legs, one of which is shown in FIG. 4 as coupling optical fiber leg 257A, in optical communication with the sensor apparatus 166'. The input leg 253 and output leg 255 can be arranged in a "feedthrough" configuration, as is known in the art.

The spectrally broadened source light from the non-linear optical element 134' can be injected into the core (e.g., a single mode core) of the input optical fiber leg 253 of the optical fiber combiner 249, which can comprise a commercially available pump and signal combiner. The single mode fiber of the input leg 253 is combined with one or more multi-mode optical fiber coupling legs 257A and 257B in the combiner section 251 of the optical fiber combiner 249. The output leg 255 of the combiner 249 can comprise double clad optical fiber which can be spliced to the length of optical waveguide 140', which can also comprise a double clad optical fiber. In certain practices of the disclosure, the output leg 255 of the combiner 249 simply also forms the length of optical waveguide 140', and no splice (indicated by "box and cross" in FIG. 4) is used. (The foregoing comment applies to FIG. 5, described below, as well).

The spectrally broadened source light can propagate within the core of the double clad fiber towards the distal end 150' of the length of optical waveguide 140, which is terminated in a beam delivery optic 256 comprising a collimating lens 260 to form a collimated optical output beam that is directed to target 154'. Within the beam delivery optic 256 some of the light is reflected and/or scattered by the collimating lens and some of this reflected light is captured within the inner cladding of the double clad fiber of the length of optical waveguide 140' and propagates within the inner cladding waveguide in an opposite direction to the spectrally broadened source light.

Alternatively or additionally, the length of optical waveguide can comprise a length of optical fiber wherein the distal end 150' of the fiber includes an end face, such as a cleave, that directs backward propagating light back up the length of optical fiber, such as into second cladding if the length of optical fiber comprises a double clad fiber. The end face can be angled, such as at an angle of several degrees (e.g., 8°) to the longitudinal axis of the fiber, to better direct the backward propagating light into the second or outer cladding of a double clad optical fiber.

On reaching the combiner section of the optical fiber combiner 251, backward propagating light guided in the double clad fiber couples to the leg 257A and hence the sensor apparatus 166'. Depending on the design of the optical fiber combiner 249, some of the backward propagating light may also couple into the leg 253. The light source 110' can include an optical isolator located to isolate one or both of the non-linear optical element and the pump source, or a component thereof, from the backward propagating light. The sensor apparatus 116' thus senses forward propagating light that has been redirected to become backward propagating light.

Typically at least one of the fiber coupler legs 257A and 257B is multimoded (more typically all are), and at least one of them is optically coupled to the sensor apparatus 166'. More than one of the coupling legs can be coupled to the same sensor apparatus 166', and/or the sensor apparatus can include a plurality of individual sensors, and the apparatus can be configured such that for at least some of the individual sensors different sensors can be coupled to different fiber coupler legs. The pump combiner 249 can include both single mode as well as multi-mode optical fibers legs, combined into a double-clad optical fiber output leg. For example, the leg 253 can be single-mode. This is one type of pump combiner which, in this invention, is particularly suited as the single mode fiber and double clad combined output of the pump combiner maintain a good beam quality of the spectrally broadened source light from the supercontinuum source 110'.

Figure 5:
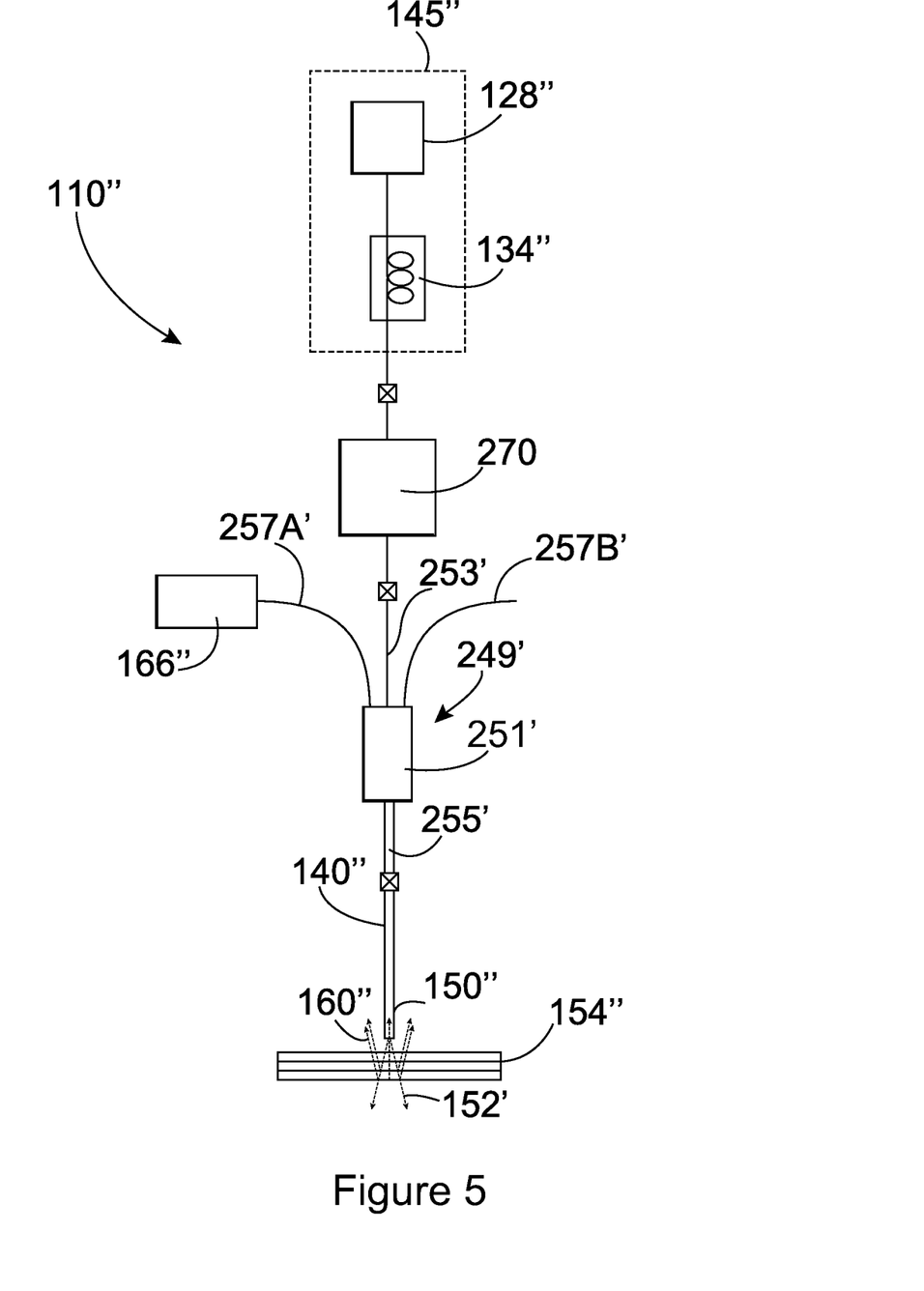
FIG. 5 schematically illustrates an additional example of an embodiment of the invention.

Optical combiner devices are commercially available from suppliers including Gooch and Housego Ltd. and others, and are typically used to combine multiple laser diodes used to pump optical fiber lasers and optical fiber amplifiers. Several types of optical combiner are known. For example, an optical fiber combiner can comprise a tapered fiber bundle. One way to form a tapered fiber bundle is to heat a bundle of fibers and pull them to a reduced diameter. See, for example, U.S. Pat. No. 5,864,644 issued to DiGiovanni et al. on Jan. 26, 1999, disclosing one type of tapered fiber bundle. Optical combiners are disclosed in, for example, U.S. Pat. No. 5,999,673, issued to Gapontsev et al. on Dec. 7, 1999; PCT application WO 2004/112206 published in the name of Sintov on Dec. 12, 2004; U.S. Pat. No. 6,434,295 issued to MacCormack et al. on Aug. 13, 2002; U.S. Pat. No. 6,826,335 issued to Grudinin et al. on Nov. 30, 2004, and U.S. Pat. No. 6,434,302 to Fidric et al. on Aug. 13, 2002. See also, as one of the earlier patents, U.S. Pat. No. 4,815,079 issued to Snitzer et al. on Mar. 21, 1989 (FIGS. 3-5). As one of ordinary skill cognizant of the present disclosure will appreciate, certain of the above combiners (e.g., U.S. Pat. No. 5,999,673) are of the side coupler type and can inherently provide better isolation between backward propagating in the feedthrough fiber and the side leg or legs. Accordingly, such combiners can be arranged such that the side leg delivers the spectrally broadened light to the output leg and the leg arranged in a feedthrough combination with the output leg is in optical communication with the sensor apparatus.

The embodiments of the light sources shown in FIGS. 2 and 4 can include an optical filter. However, for brevity this filter is described in conjunction with FIG. 5, though the skilled worker will readily appreciate that the discussion is equally applicable to the embodiments shown in FIGS. 2 and 4.

The output leg 255 of the optical fiber combiner can be a multi-mode optical fiber which delivers the spectrally broadened source light to the length of optical waveguide, such as to the core of a length of optical fiber of the optical waveguide. The optical fiber can be a single clad or double clad fiber, and/or the core of the fiber can comprise a multimode core. The multimode core of the fiber can be configured to receive the backward propagating light and the coupling leg 257A of the optical fiber combiner can couple backward propagating light to the sensor apparatus 166'. The foregoing may result in lower beam quality of the exit beam 152', which is sometimes acceptable.

The broadband or tunable output light from a supercontinuum laser is ideal for carrying out spectroscopic or high resolution interferometric analysis of a target. The broadband light can be delivered directly, or filtered or swept through particular wavelengths (by a tunable filter) to provide light in the visible or near infrared region of the spectrum for illuminating a sample. The light scattered or reflected from the sample can then be analysed (wavelength, phase, amplitude, time of flight, etc).

In conventional film-thickness measurement instruments relying on white-light interferometry (see, for example, WO 2010/001165 A1), a high power lamp source is used as the illumination source. The output from this lamp is launched into a bundle of optical fibers with extremely low launch efficiency due to the relatively low optical brightness of the lamp and the small effective aperture and low fill-factor of the waveguide sections of the fiber bundle. Furthermore, reflected light from the sample under test back into fiber bundles is even less efficient, meaning that the detected light levels are minute, requiring long integration times necessary to achieve a low-noise and accurate measurement and diagnosis of the interferogram. As target sample sizes become larger or as scanning rates increase, there is a requirement to increase the power delivered to and captured from the sample in order to reduce integration times.

The light sources described herein are considered to provide an improved means for both delivering light to the sample, and collecting reflected light from the sample so as to deliver the light to a sensor, such as, for example, a spectrometer instrument for analyzing the reflected light. The high brightness available from a supercontinuum laser source allows for better illumination and also more efficient capture of reflected light from the sample under investigation—increasing signal to noise, reducing the power required from the illumination source and increasing the speed at which images and measurements can be taken.

Accordingly, FIG. 5 schematically illustrates another embodiment of the present disclosure, wherein a light source forms part of an instrument to measure film thickness by way of white-light interferometry. The light source 110" can be the same as those described above, as indicated at times by the use the same reference numerals (distinguished with primes and double primes), with certain distinctions now discussed.

With reference to FIG. 5, spectrally broadened source light is injected into a single mode optical fiber input leg of pump combiner 251' and is delivered to the distal end 150" of the length of optical waveguide 140" within the core of a double clad fiber comprised by the length of optical waveguide. The distal end 150" of the double clad fiber is terminated with a cleaved end and is positioned in close proximity to the target sample 154". The sample 154" is preferably partially transparent to the spectrally broadened source light and typically comprises one or more layers or surfaces having partial reflectivity.

Some of the partially reflected light from the different surfaces or layers is collected within the inner cladding waveguide of the double clad fiber and backward propagated in the opposite direction to the spectrally broadened source light towards the pump combiner 251' for sensing by the sensor apparatus 166". The sensor apparatus comprises a spectrometer which spectrally analyses the reflected light from the different layers of the sample under test and to observe the interference patterns due to light reflected from adjacent layers or surfaces, thus providing a measurement of surface separation and/or layer thickness.

As noted above, a light source according to the disclosure can include a filter. Shown in FIG. 5 is a filter component 270 which can filter spectrally broadened light before the delivery thereof to the combiner from the non-linear optical element 134". The filter component can be a fixed bandpass, short pass or long pass filter or can alternatively be a programmable or swept filter such that the spectrum of the spectrally broadened light, and thus the spectrum of the output light beam that illuminations the target sample 154", can be adjusted or controlled.

The length of optical waveguide (140, 140', 140") in the foregoing embodiments can comprise a length of optical fiber that is bundled with other lengths of optical fiber. Some or all of the other lengths of optical fiber can collect light reflected, scattered, radiated, etc. from a sample and be configured for communicating such light (160, 160', 160") to the sensor apparatus, such as to one or more sensors of the sensor apparatus.

The foregoing disclosure is by way of example and not limitation. Those of ordinary skill in the art will readily envision a variety of other means and structures for performing the functions and/or obtaining the results or advantages described herein and each of such variations or modifications is deemed to be within the scope of the present invention. More generally, those skilled in the art would readily appreciate that all parameters, dimensions, materials and configurations described herein are meant to be exemplary and that actual parameters, dimensions, materials and configurations will depend on specific applications for which the teachings of the present invention are used.

Generally speaking it is to be understood that unless a specific explicit statement is made to the contrary herein or it is evident to the skilled worker that certain features are mutually exclusive (e.g., where the feature of one embodiment is a feature that distinguishes one species of a genus from a mutually exclusive feature of another species of the genus, where the other species is illustrated as a separate embodiment) features shown herein in conjunction with one embodiment can be included in another of the disclosed embodiments. For example, the embodiments shown in FIGS. 2 and 4 can include a filter, such as the filter 270 shown in the embodiment of FIG. 5; the embodiments shown in FIGS. 2 and 5 can include the beam delivery optic and/or an angled cleaved end face as is described generally in conjunction with the embodiment of FIG. 4 (beam delivery optic 256), though some changes may be made (such as, for example, in the design of the beam delivery optic) such that light scattered from the target is primarily sensed; the embodiment of FIG. 2 can include a beam combiner as is described in conjunction with FIG. 4 (beam combiner 251) or FIG. 5 (beam combiner 251'); or the embodiments of FIG. 4 of FIG. 5 can include the a sensor as described in conjunction with FIG. 2 (sensor 66).

Those skilled in the art will recognize or be able to ascertain using no more than routine experimentation many equivalents to the specific embodiments of the invention described herein. It is therefore to be understood that the foregoing embodiments are presented by way of example only and that within the scope of the appended claims, and equivalents thereto, the invention may be practiced otherwise than as specifically described.

In the claims as well as in the specification above all transitional phrases such as "comprising", "including", "carrying", "having", "containing", "involving" and the like are understood to be open-ended. Only the transitional phrases "consisting of" and "consisting essentially of" shall be closed or semi-closed transitional phrases, respectively, as set forth in the U.S. Patent Office Manual of Patent Examining Procedure §2111.03, 7$^{th}$ Edition, Revision 1. Furthermore, statements in the specification, such as, for example, definitions, are understood to be open ended unless otherwise explicitly limited.

The phrase "A or B" as in "one of A or B" is generally meant to express the inclusive "or" function, meaning that all three of the possibilities of A, B or both A and B are included, unless the context clearly indicates that the exclusive "or" is appropriate (i.e., A and B are mutually exclusive and cannot be present at the same time). "At least one of A, B or C" (as well as "at least one of A, B and C") reads on any combination of one or more of A, B and C, including, for example the following: A; B; C; A & B; A & C; B & C; A & B; as well as on A, B & C.

It is generally well accepted in patent law that "a" means "at least one" or "one or more." Nevertheless, there are occasionally holdings to the contrary. For clarity, as used herein "a" and the like mean "at least one" or "one or more." The phrase "at least one" may at times be explicitly used to emphasize this point. Use of the phrase "at least one" in one claim recitation is not to be taken to mean that the absence of such a term in another recitation (e.g., simply using "a") is somehow more limiting. Furthermore, later reference to the term "at least one" as in "said at least one" should not be taken to introduce additional limitations absent express recitation of such limitations. For example, recitation that an apparatus includes "at least one widget" and subsequent recitation that "said at least one widget is coloured red" does not mean that the claim requires all widgets of an apparatus that has more than one widget to be red. The claim shall read on an apparatus having one or more widgets provided simply that at least one of the widgets is coloured red. Similarly, the recitation that "each of a plurality" of widgets is coloured red shall also not mean that all widgets of an apparatus that has more than two red widgets must be red; plurality means two or more and the limitation reads on two or more widgets being red, regardless of whether a third is included that is not red, absent more limiting explicit language (e.g., a recitation to the effect that each and every widget of a plurality of widgets is red).

What is claimed is:

1. Optical supercontinuum apparatus, comprising:
   a pump laser for providing pump pulses;
   a non-linear optical element in optical communication with the pump laser, the non-linear optical element configured for generating spectrally broadened light responsive to the pump pulses and one or more non-linear processes, said non-linear optical element comprising a length of optical waveguide;
   an optical output for delivering spectrally broadened light to a target;
   said length of optical waveguide optically upstream of said output and in optical communication therewith, said length of optical waveguide comprising at least a first waveguiding region, said first waveguiding region configured for propagating the spectrally broadened light in a forward direction, the forward direction being toward said output;
   said length of optical waveguide further configured for receiving backward propagating light responsive to the spectrally broadened forward propagating light, "backward" meaning being in a direction opposite to said forward propagating light; and
   sensor apparatus configured for optical communication with said length of optical waveguide so as to sense the backward propagating light propagated by said length of optical waveguide.

2. The optical supercontinuum apparatus of claim 1 wherein said length of optical waveguide comprises a second waveguiding region that is different than said first waveguiding region, said second waveguiding region for receiving and propagating the backward propagating light.

3. The optical supercontinuum apparatus of claim 2 wherein said second waveguiding region is configured to support substantially more spatial modes than said first waveguiding region.

4. The optical supercontinuum apparatus of claim 2 wherein said length of optical waveguide comprises a double clad fiber having a core, an inner cladding disposed about said core, and an outer cladding disposed about said inner cladding, said first waveguiding region comprising said core and said second waveguiding region comprising said inner cladding.

5. The optical supercontinuum apparatus of claim 2 wherein said first waveguiding region is single mode over at least part of the full width half maximum (FWHM) wavelength range of the spectrum of spectrally broadened light generated by said non-linear optical element and wherein said second waveguiding region is multimode over at least part of the same wavelength range.

6. The optical supercontinuum apparatus of claim 2 wherein said second waveguiding region has a numerical aperture of at least 0.4.

7. The optical supercontinuum apparatus of claim 2 wherein the material of said first and second waveguiding regions consists essentially of undoped silica glass.

8. The optical supercontinuum apparatus of claim 1 wherein said sensor apparatus comprises a photodetector.

9. The optical supercontinuum apparatus of claim 1 wherein said sensor apparatus comprises an optical spectrum analyzer.

10. The optical supercontinuum apparatus of claim 1 configured such that said length of optical waveguide spectrally broadens light propagated thereby in the forward direction.

11. The optical supercontinuum apparatus of claim 1 wherein said pump laser comprises a pulsed fiber laser producing pump pulses having a FWHM time duration that is in the range from 1 ps to 500 ps.

12. The optical supercontinuum apparatus of claim 1 wherein said pump laser comprises a laser fiber laser cavity comprising a semiconductor saturable absorber mirror (SESAM) mode locking element and a length of rare earth doped optical fiber.

13. The optical supercontinuum apparatus of claim 12 wherein said length of rare earth doped optical fiber has normal dispersion at its wavelength of operation.

14. The optical supercontinuum apparatus of claim 1 wherein said non-linear optical element comprises a length of microstructured fiber having a core and a plurality of longitudinally extending features disposed about said core.

15. The optical supercontinuum apparatus of claim 14 wherein said microstructured optical fiber does not guide light via a photonic bandgap effect and said core does comprise an endlessly single mode core.

16. The optical supercontinuum apparatus of claim 14 wherein said core of said microstructured optical fiber comprises a diameter of no less than 2 microns and no greater than 6 microns and a numerical aperture of no less than 0.12 and no greater than 0.35, and wherein said microstructered optical fiber includes a microstructured region disposed about said core and comprising said longitudinally extending features, said microstuctered region comprising an air-fill fraction of at least 0.5.

17. The optical supercontinuum apparatus of claim 1 comprising an optical fiber combiner optically interposed between said length of optical waveguide and said sensor apparatus and configured for coupling backward propagating light from said length of optical waveguide for provision to said sensor apparatus.

18. The optical supercontinuum apparatus of claim 17 wherein said optical fiber combiner comprises first and second optical fiber legs arranged in a feedthrough configuration and at least one side coupling optical fiber leg, said side coupling optical fiber leg being in optical communication with said non-linear optical element for receiving spectrally broadened light and coupling the spectrally broadened light to the first optical fiber leg, said first optical fiber leg in optical communication with said length of optical waveguide and said second optical fiber leg in optical communication with said sensor apparatus.

19. The optical supercontinuum apparatus of claim 1 wherein said non-linear element further comprises a length of optical fibre and wherein said length of optical waveguide comprises at least one more cladding than said non-linear optical element.

20. The optical supercontinuum apparatus of claim 1 wherein said non-linear optical element further comprises a length of optical fiber, and wherein said apparatus is configured such that said length of optical waveguide propagates the forward propagating spectrally broadened light in substantially more spatial modes than said length of optical fiber.

21. The optical supercontinuum apparatus of claim 20 wherein said length of optical fiber propagates spectrally broadened light in substantially a single spatial mode.

22. The optical supercontinuum apparatus of claim 1 wherein said non-linear optical element comprises an optical element, optically upstream of said length of optical waveguide, that also provides spectral broadening.

23. The optical supercontinuum apparatus of claim 1 wherein said nonlinear optical element comprises a selected length of optical fiber and wherein said length of optical waveguide comprises said selected length of optical fiber.

24. A method of operating a source of supercontinuum laser pulses, comprising:
optically pumping a length of optical waveguide with optical pump pulses to generate spectrally broadened light via one or more non-linear processes;
propagating the spectrally broadened light in a forward direction along the length of optical waveguide for eventual delivery to an output;
receiving, responsive to the forward propagating spectrally broadened light, backward propagating light with the length of optical waveguide; and
sensing the backward propagating light with a sensor apparatus in optical communication with the length of optical waveguide so as to receive backward propagating light.

25. The method of claim 24 comprising changing a property of the spectrally broadened light output from the output responsive to the sensing of the backward propagating light.

26. The method of claim 24 wherein sensing the backward propagating light comprises sensing the backward propagating light so as to determine a property of the forward propagating spectrally broadened light.

27. The method of claim 24 comprising redirecting, optically upstream of the output, forward propagating spectrally broadened light so as to become backward propagating and wherein at least the majority of the optical power sensed by the sensor apparatus is due to such redirected forward propagating light.

28. The method of claim 24 wherein optically pumping the length of optical fiber comprises optically pumping the length of optical fiber with pulses having a time duration in the range from 1 ps to 250 ps, a wavelength in the range from 900 nm to 1200 nm, and wherein the length of optical fiber comprises a zero dispersion wavelength in the range of 900 nm to 1200 nm.

29. The method of claim 24 wherein propagating spectrally broadened light in the forward direction comprises propagating the spectrally broadened light with a first waveguiding region of the length of optical waveguide and wherein receiving the backward propagating light comprises receiving the backward propagating light with a second waveguiding region of the length of optical waveguide, wherein the second waveguiding region does not substantially propagate forward propagating spectrally broadened light.

30. The method of claim 24 wherein receiving backward propagating light comprises receiving backward propagating light from a target to which light from the output has been directed.

* * * * *